United States Patent
Grant et al.

(10) Patent No.: US 10,398,908 B2
(45) Date of Patent: Sep. 3, 2019

(54) ELECTROMAGNETIC RADIATION TECHNIQUES FOR IN VIVO TISSUE

(71) Applicant: STRATHSPEY CROWN HOLDINGS, LLC, Newport Beach, CA (US)

(72) Inventors: Robert Edward Grant, Laguna Beach, CA (US); Matthew T. Case, Laguna Hills, CA (US)

(73) Assignee: Strathspey Crown Holdings, LLC, Newport Beach, CA (US)

( * ) Notice: Subject to any disclaimer, the term of this patent is extended or adjusted under 35 U.S.C. 154(b) by 888 days.

(21) Appl. No.: 14/854,935

(22) Filed: Sep. 15, 2015

(65) Prior Publication Data
US 2017/0072215 A1   Mar. 16, 2017

(51) Int. Cl.
*A61N 5/06* (2006.01)
*A61H 23/00* (2006.01)
*A61N 5/067* (2006.01)

(52) U.S. Cl.
CPC ............. *A61N 5/06* (2013.01); *A61H 23/008* (2013.01); *A61N 5/0601* (2013.01); *A61H 2201/10* (2013.01); *A61N 2005/063* (2013.01); *A61N 2005/067* (2013.01)

(58) Field of Classification Search
CPC .. A61N 5/06; A61N 5/0601; A61N 2005/067; A61N 2005/063; A61H 23/008; A61H 2201/10
See application file for complete search history.

(56) References Cited

U.S. PATENT DOCUMENTS

| | | |
|---|---|---|
| 4,686,127 A | 8/1987 | Burns et al. |
| 6,024,690 A | 2/2000 | Lee et al. |
| 6,033,357 A | 3/2000 | Ciezki et al. |
| 6,077,213 A | 6/2000 | Ciezki et al. |
| 6,221,094 B1 | 4/2001 | Bare |
| 6,309,339 B1 | 10/2001 | Ciezki et al. |
| 6,521,210 B2 | 2/2003 | Ohkawa |
| 6,626,816 B1 | 9/2003 | Ciezki et al. |
| 6,725,081 B2 | 4/2004 | Ciezki et al. |
| 7,280,874 B2 | 10/2007 | Boehm |
| 7,418,294 B2 | 8/2008 | May |
| 7,500,956 B1 | 3/2009 | Wilk |

(Continued)

OTHER PUBLICATIONS

Dubost, G. and Bellosi, A., "Efficiency of Solitary waves Radiated by the Discharged in a Confined Plasma Column", Oct. 2004, p. 473 to 481. Biological Effects of EMFS, 3rd Intern. Workshop Kos, Greece. (Year: 2004).*

(Continued)

*Primary Examiner* — Quang D Thanh
(74) *Attorney, Agent, or Firm* — Fish IP Law, LLP

(57) ABSTRACT

A system and method for using a sonic wave to influence material in a target structure requires using a confined plasma antenna to generate an electromagnetic carrier wave, $\lambda$. The confined plasma antenna also pulses the carrier wave at a sonic frequency, f, to create a sonic wave. In detail, pulsing the carrier wave results in a sequential plurality of solitons which are separated from each other by a periodicity $\rho$, wherein $\lambda<<\rho$. For the present invention, f is selected to resonate with a material (e.g. a cellular structure) in a target structure (e.g. a patient).

7 Claims, 1 Drawing Sheet

(56) References Cited

U.S. PATENT DOCUMENTS

| | | |
|---|---|---|
| 8,326,408 B2 | 12/2012 | Green et al. |
| 8,440,154 B2 | 5/2013 | Fahs, II et al. |
| 8,591,419 B2 | 11/2013 | Tyler |
| 2004/0030370 A1* | 2/2004 | Lytle .................... A61N 5/0616 607/89 |
| 2004/0097841 A1* | 5/2004 | Saveliev .............. A61H 9/0078 601/15 |
| 2009/0005631 A1* | 1/2009 | Simenhaus ............ A61N 2/002 600/9 |
| 2011/0125226 A1* | 5/2011 | Lytle .................... A61N 5/0613 607/88 |

OTHER PUBLICATIONS

Dubost, G. and Bellossi, A., "Experimental Approach of the Electromagnetic Effects in Vivo Due to the Solitary-Waves Radiated by a Confined Plasma Antenna", The Second European Conference on Antennas and Propagation, Nov. 11-16, 2007, EuCAP 2007, Publisher: IET.

* cited by examiner

ELECTROMAGNETIC RADIATION TECHNIQUES FOR IN VIVO TISSUE

FIELD OF THE INVENTION

The present invention pertains generally to systems and methods for generating, in combination, an electromagnetic wave having a wavelength λ and a sonic wave having a frequency f, for simultaneous transmission of these waves on a same beam path for incidence on a target structure. More particularly, the present invention pertains to systems and methods that pulse an electromagnetic carrier wave at a controlled sonic frequency f to create solitons on the carrier wave. The present invention is particularly, but not exclusively, useful as a system and method for influencing material in a target with a sonic wave, when the sonic wave is created by solitons that are carried on an electromagnetic wave and the frequency f of the sonic wave is selected to resonate with a specified material in the target structure.

BACKGROUND OF THE INVENTION

Electromagnetic waves and sonic waves are both well known. From a very simplistic perspective, although both wave types will radiate through a medium and can be characterized by a periodicity, they otherwise have very profound differences. Interestingly, they are referred to by different physical characteristics. For instance, electromagnetic waves (e.g. light wave) are typically identified by their wavelength, λ (i.e. their period). On the other hand, though sonic waves also have a period, sonic waves are typically identified by their frequency, f (i.e. period/time). In comparison, a wavelength λ for light is very much less than the period ρ of a sonic wave (λ<<ρ).

Insofar as wave types are concerned, of interest for the present invention is a physical phenomenon known as a solitary-wave, or soliton. A soliton is a very specific type of self-reinforcing waveform that has several unique characteristics. Technically, these characteristics can result when non-linearity and dispersion effects, on a wave that is traveling in a medium, interact with (i.e. cancel) each other. The characteristics of a soliton include: a constant shape that does not change over time; a constant energy (self-reinforcing); and a localized effect within a region. Of particular interest for the present invention are solitons that are created on a wave of electromagnetic radiation.

An example of a device for generating solitons (solitary-waves) on an electromagnetic wave is provided in an article by G. Dubost and A. Bellossi entitled "Experimental Approach of the Electromagnetic Effects In Vivo due to the Solitary-Waves Radiated by a Confined Plasma Antenna" which was published November 2007, at The Second European Conference on Antennas and Propagation (pages 1-5, Conference on Nov. 11-16, 2007). The Dubost/Bellossi article further discloses the observation that electromagnetic waves can interact with the amplitude of electric fields in surface waves (e.g. Zeneck waves) on a living medium for in vivo reradiation of the electromagnetic waves by nervous fibers.

In addition to the above, it is also known that various waveforms, both light waves and sonic waves, are capable of influencing matter. In particular U.S. patent application Ser. No. 14/488,101, filed on Sep. 16, 2014 for an invention entitled "System and Method for Using Sonic Radiation to Influence Cellular Structure", and U.S. patent application Ser. No. 14/632,941, filed on Feb. 26, 2015 for an invention entitled "System and Method for Using Electromagnetic Radiation to Influence Cellular Structure", both of which are assigned to the same assignee as the present invention, provide respective disclosures for using waveforms to influence matter.

With the above in mind, it is an object of the present invention to generate an electromagnetic/sonic-soliton wave for the purpose of influencing matter (e.g. a cellular structure). Another object of the present invention is to provide a system and method for influencing material in a target with a sonic wave, when the sonic wave is created by a plurality of solitons having a frequency f, when the sonic wave is carried on an electromagnetic wave, and the frequency f of the sonic wave is selected to resonate with a specified material in the target structure. Still another object of the present invention is to provide a system and method for influencing material in a target with an electromagnetic/sonic-soliton wave that is easy to implement, is simple to operate and is comparatively cost effective.

SUMMARY OF THE INVENTION

In accordance with the present invention, a system for using electromagnetic radiation to generate sonic waves for the purpose of influencing target material (e.g. a cellular structure) includes, in combination, a confined plasma antenna, a waveguide, and a modulator. In detail, the confined plasma antenna is used for generating a sequential plurality of solitons. For the present invention, each soliton in the plurality is generated as a pulse on an electromagnetic carrier wave having a wavelength λ. Importantly, each soliton has a constant shape and they all are generated by the confined plasma antenna at a controlled frequency f. Further, the controlled frequency f is a sonic frequency. The result is the creation of an Electronic/Sonic-Soliton wave (sometimes hereinafter referred to as an E/S-S wave).

In its combination with the confined plasma antenna, the waveguide is provided to direct the plurality of solitons as a sonic wave carried by the electromagnetic carrier wave along a beam path toward a target. As envisioned for the present invention, the waveguide can be of any type well known in the pertinent art. For instance, when the electromagnetic carrier wave is a laser beam having the wavelength λ, the waveguide may be an optical fiber. Another possibility is that the waveguide may be a directional antenna.

The modulator, which is connected directly with the confined plasma antenna, is provided to establish and control operational parameters for the E/S-S wave, such as f and λ. Specifically, the parameters for f and λ are selected to influence material in the target. As envisioned for the present invention, f will typically be a resonant frequency of a material in the target. Further, when the target is a living body (e.g. a patient) λ will typically be established by the modulator based on the frequency and electric field amplitude of selected surface waves on the target.

A methodology for generating sonic waves using electromagnetic radiation in accordance with the present invention requires creating a beam of electromagnetic radiation having a wavelength λ. Specifically, the beam of electromagnetic radiation is created for use as a carrier wave. Next, the carrier wave (i.e. the electromagnetic radiation beam) is pulsed at a controlled frequency f to generate a plurality of solitons on the carrier wave. In this case, each soliton will have a constant shape and the controlled frequency f will be a sonic frequency. Then, the plurality of solitons are directed as a sonic wave along a beam path of the carrier wave toward a target. As a setup, operational parameters for f and λ are established to influence material in the target.

DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENT

Figure 1:
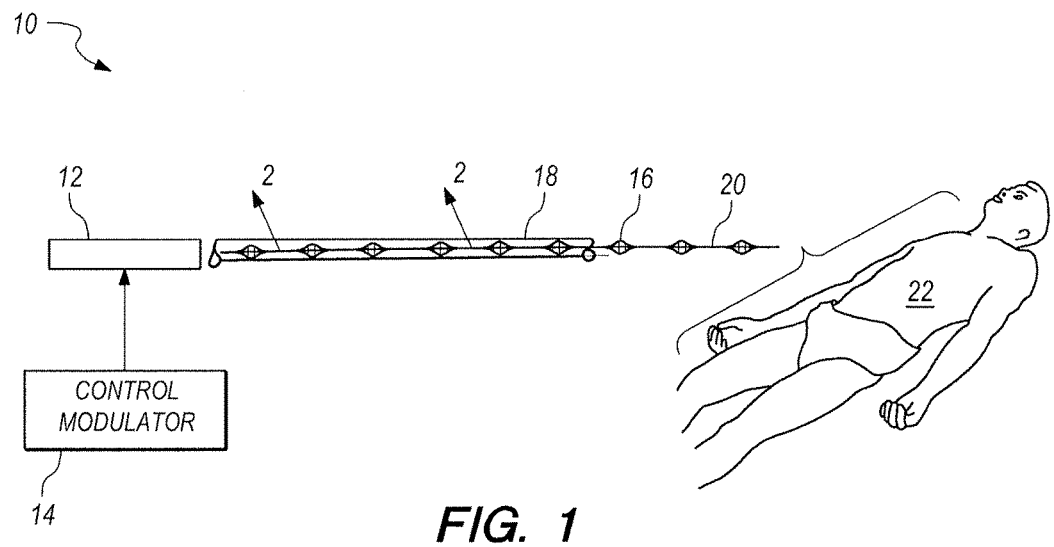
FIG. 1 is a schematic presentation of the components of the present invention in their intended operational environment.

Referring initially to FIG. 1, a system in accordance with the present invention is shown and is generally designated 10. As shown, the system 10 includes a confined plasma antenna 12 which is controlled by a modulator 14 to generate an electromagnetic/sonic-soliton beam 16. Further, the system can optionally include a waveguide 18 which will direct the electromagnetic/sonic-soliton beam 16 along a beam path 20 toward a target, such as the patient 22. As envisioned for the present invention, the waveguide 18 can be of any type well known in the pertinent art. For instance, when the ES-S wave 16 incorporates a laser as its the carrier, the waveguide 18 may be an optical fiber. In any event, as indicated in FIG. 1, the waveguide 18 is intended to have the capability of radiating all, or selected portions, of the target (patient 22).

Figure 2:
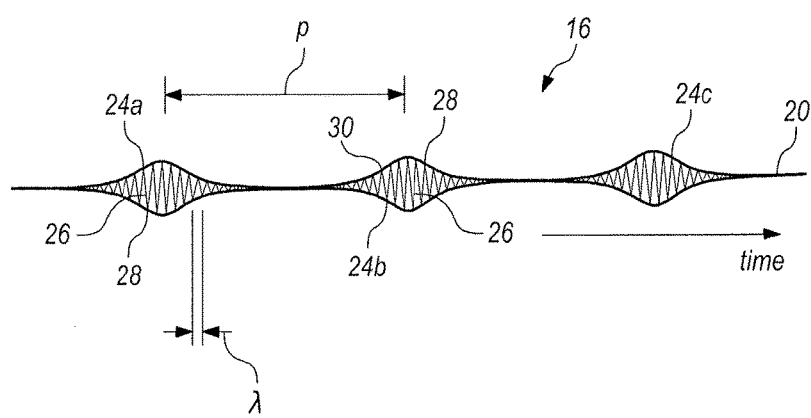
FIG. 2 is a cross-section view of the electromagnetic/sonic-soliton beam generated in accordance with the present invention.

As shown in FIG. 2, an electromagnetic/sonic-soliton beam 16 is shown to include a plurality of solitons 24, of which the solitons 24a, 24b and 24c are exemplary. Further, it will be seen that the electromagnetic/sonic-soliton beam 16 is based on an electromagnetic radiation 26 which has a wavelength λ, and effectively acts as a carrier for a sonic wave 28.

Operationally, the sonic wave 28 is created by pulsing the electromagnetic wave 26 at a sonic frequency f, prior to a radiation of the electromagnetic/sonic-soliton beam 16 from the confined plasma antenna 12. As intended for the present invention, pulsing of the electromagnetic wave 26 is accomplished with a periodicity ρ for the sonic frequency f. As indicated in FIG. 2, λ is very much shorter than ρ. The result of all this is that each soliton 24 is contained within a defining envelope 30 that effectively acts as a sonic wave 28. Thus, each soliton 24, in sequence with other solitons 24, can be directed onto a target/patient 22 to influence material (e.g. cellular structure) in the target/patient 22 as the sonic wave 28.

What is claimed is:

1. A system for using electromagnetic radiation to generate sonic waves which comprises:
   a confined plasma antenna that generates an electromagnetic/sonic-soliton beam comprising a plurality of solitons, wherein each soliton is characterized as a pulse in a carrier wave of electromagnetic radiation, wherein the electromagnetic radiation has a wavelength λ and each soliton has a constant shape, wherein the solitons are generated in the carrier wave at a controlled frequency f, and
   further wherein the controlled frequency f is a sonic frequency;
   a waveguide connected with the confined plasma antenna for directing the plurality of solitons as a sonic wave carried by the carrier wave along a beam path toward a target; and
   a modulator connected with the confined plasma antenna to establish
   operational parameters for f and λ to influence material in the target.

2. The system as recited in claim 1 wherein the controlled frequency f is a resonant frequency of the material in the target.

3. The system recited in claim 1 wherein the electromagnetic radiation is a laser beam having the wavelength λ.

4. The system recited in claim 3 wherein the wavelength λ is established by the modulator based on a frequency and amplitude of an electric field of a surface wave on the target.

5. The system recited in claim 3 wherein an amplitude for the wavelength λ is established by the modulator.

6. The system as recited in claim 1 wherein the waveguide includes an optical fiber.

7. The system as recited in claim 1 wherein the target is tissue in a cellular structure.

* * * * *